United States Patent [19]

Ehr et al.

[11] Patent Number: 5,323,846
[45] Date of Patent: Jun. 28, 1994

[54] FLUID CIRCULATOR AND TEMPERATURE REGULATOR

[75] Inventors: Timothy G. J. Ehr, Menomonee Falls; Michael E. Hansen, Pewaukee, both of Wis.

[73] Assignee: Fotodyne Incorporated, Hartland, Wis.

[21] Appl. No.: 820,529

[22] Filed: Jan. 14, 1992

[51] Int. Cl.$^5$ .............................................. F28D 15/00
[52] U.S. Cl. ................................. 165/104.32; 165/71; 165/95; 204/299 R
[58] Field of Search ................ 165/104.32, 95, 71; 204/299 R

[56] References Cited

U.S. PATENT DOCUMENTS

| | | | |
|---|---|---|---|
| 2,041,241 | 5/1936 | Goldfield | 165/104.32 |
| 3,989,102 | 11/1976 | Jaster et al. | 165/104.32 |
| 4,592,418 | 6/1986 | Cadars | 165/104.32 |
| 4,612,106 | 9/1986 | Kromer et al. | 204/299 |
| 5,158,661 | 10/1992 | Hansen | 204/299 R |

FOREIGN PATENT DOCUMENTS

| | | |
|---|---|---|
| 287513 | 10/1988 | European Pat. Off. |
| 636525 | 5/1950 | United Kingdom |
| 952195 | 3/1964 | United Kingdom |
| 2236842 | 4/1991 | United Kingdom |

OTHER PUBLICATIONS

Neslab 1992 catalog, pp. 3–34, published 1991.
Cole-Parmer catalog.
Techne 1991/92 catalog, pp. 3–7, published 1991.
Lauda catalog, published 1984.
Grant catalog, pp. 4–7, 11–13, published 1991.
Tekmar 91/92 catalog, pp. 33, 34.

Primary Examiner—Albert W. Davis, Jr.
Attorney, Agent, or Firm—Michael, Best & Friedrich

[57] ABSTRACT

A fluid circulator and temperature regulator apparatus for use in an electrophoresis process with a sequencing cell including a cooling jacket having an inlet and an outlet, the apparatus being adapted to be connected to the cooling jacket inlet and outlet, and the apparatus comprising a reservoir, a pump for circulating cooling fluid through the cooling jacket, and a heat exchanger for regulating the temperature of the cooling fluid, the apparatus being operable for filling and draining the reservoir, for degasifying fluid in the reservoir, and for filling and draining the cell.

10 Claims, 7 Drawing Sheets

FLUID CIRCULATOR AND TEMPERATURE REGULATOR

FIELD OF THE INVENTION

The invention relates to apparatus used in gel electrophoretic separations of DNA molecules, protein and other charged molecules. This is commonly referred to as DNA sequencing apparatus or electrophoresis apparatus. More particularly, the invention relates to devices employed with electrophoresis apparatus to circulate fluids through a sequencing cell and to regulate the temperature of such fluids.

BACKGROUND OF THE INVENTION

A known electrophoresis apparatus includes a sequencing cell with a cooling jacket, a power supply, and a device for circulating coolant through the cooling jacket. This device includes a temperature-controlled water bath and a pump for circulating water through the cooling jacket.

Most temperature controlling baths associated with laboratory equipment are structured to circulate a fluid (typically water) within the confines of a bath. The circulator functions to move the working fluid past the heating and/or cooling coils, and achieve a uniform bath temperature.

Additionally, circulation units designed to pass thermostatically controlled liquid through jacketed equipment and closed vessels are common in the art. Such devices are often substantially identical to the above baths with the additional inclusion of circulating ports. A pump is generally, but not always, included in the apparatus to perform the circulating function. Some provide pressure or suction capabilities to the external equipment to be cooled. Such devices, like the baths above, use compressor based refrigeration to achieve temperatures below ambient.

With known circulation units it is necessary to disconnect the unit from the cell in order to drain the cell.

SUMMARY OF THE INVENTION

The invention provides a thermal regulator that circulates cooling water or fluid through a sequencing cell and that regulates the temperature of the cooling fluid. The thermal regulator includes a microprocessor controlled liquid-to-air heat exchanger. Heating and cooling is done with thermoelectric modules. Pumping of fluid is by an oscillating pump. Path of fluid flow is controlled by two solenoid valves. Fluid is contained in a reservoir internal to the unit.

Thermoelectric heat pumps are solid state chips that pump heat in either direction (heating or cooling) dependent on the direction of current flow through the chips. Direction of current flow is controlled by the microprocessor. The temperature of the liquid can be set from 20.0° to 50.0° C. The microprocessor maintains the fluid at the set temperature by reading the temperature of the fluid (by thermistor) and controlling both the direction and level of current to the thermoelectrics. The microprocessor utilizes an algorithm (PID LOOP) to compare the temperature set point to the actual fluid temperature and determine a current level and direction for the thermoelectrics. Actual temperature of the fluid can also be displayed on the front panel.

Fluid flow rate is controlled by adjusting the speed of the fluid pump. The microprocessor controls the speed of the pump by controlling the phase angle of a half-wave rectified sine wave. The flow rate of the pump is user-programmable by keys and a display on the front panel.

The path of fluid flow is controlled by two solenoid valves. There are three basic paths: bypass (degas); run-cell (external); and empty-cell.

In bypass mode the unit is only circulating fluid internal to the unit. The reason for this is to elevate the temperature of the fluid so that gas can escape the fluid before the fluid is fed to the electrophoresis cell.

In run-cell mode, the fluid is circulated externally to the electrophoresis cell. An alternative use for this mode is to empty the reservoir of fluid. This is done by disconnecting the cell from the inlet and outlet ports and connecting a tube to the outlet port. Fluid can then be removed from the unit in this mode. The reservoir would be emptied for cleaning or transportation.

The purpose of the empty-cell mode is to remove the fluid from the cell (replaced with air) and put it back in the reservoir. An alternative use for this mode is to fill the reservoir. To fill the reservoir, a tube is connected to the intake port. Water (fluid) is drawn into the unit by this tube and is circulated through the cell and into the reservoir. Air is exited through the top of the reservoir through a tube out the back of the unit.

The fluid path or mode is user-programmable by keys and a display on the front panel. The microprocessor controls the solenoids.

An interlock connector is controlled by the microprocessor. The interlock connector is a switch that is normally closed when the thermal regulator is in run-cell mode and that is open when the regulator is in any other mode. The interlock connector or switch is connected to the 10 KV power supply. If the interlock switch is closed, the 10 KV power supply will recognize this and output its voltage. If the switch is open, no voltage is output to the sequencing cell. Thus, the cell cannot be powered unless the thermal regulator is in run-cell mode. The interlock thereby prevents the user from ruining the run by forgetting to switch the thermal regulator to run-cell mode.

Two limit switches are located in the reservoir, one a low-limit switch and the other a high-limit switch. The microprocessor will recognize the high limit and shut off the pump. This could only happen when the user is filling the reservoir. If fluid flow does not shut off, the reservoir will overflow and water will exit the reservoir through the vent. When the low limit is recognized by the microprocessor, it disables the interlock switch (and thereby shuts off the power supply) and shuts off the pump. If the reservoir were emptied of fluid and the pump continued to operate, air would enter the cell and possibly ruin the run.

An advantage of the thermal regulator is that the degas and empty-cell modes are operable while the regulator is connected to the sequencing cell. The degas mode also operates while the regulator is disconnected from the cell.

Another advantage of the thermal regulator is that it pumps fluid under pressure to the cell. This eliminates induced bowing of the cell plates, which risk is present if the cooling fluid is sucked out of the cooling jacket.

Another advantage of the thermal regulator is that cooling fluid is pumped out of the cooling jacket rather than, as with known systems, simply flowing out due to gravity when the fluid circulator is disconnected from the cell.

Figure 1:
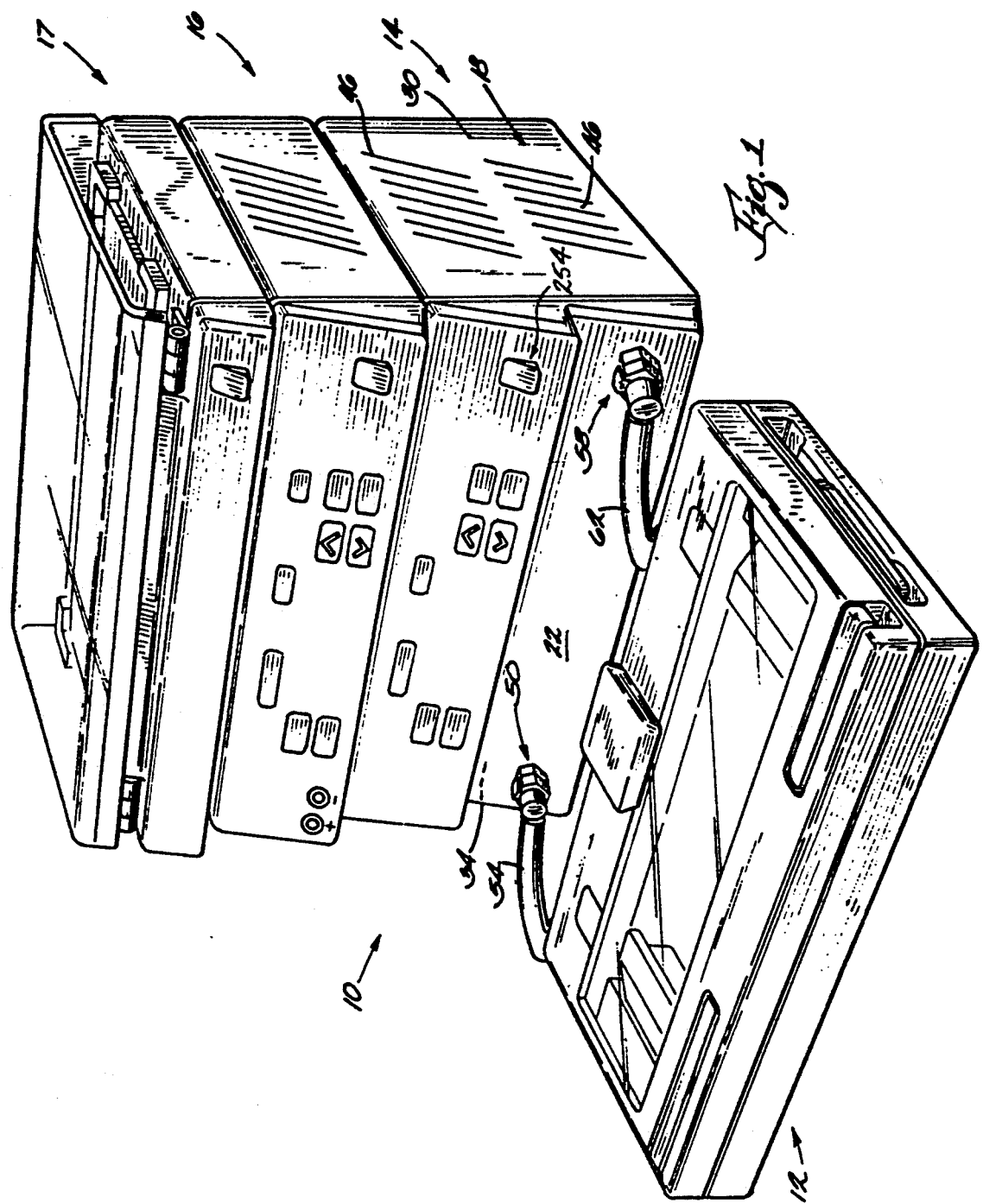
FIG. 1 is a perspective view of an electrophoresis apparatus embodying the invention.

Before one embodiment of the invention is explained in detail, it is to be understood that the invention is not limited in its application to the details of the construction and the arrangements of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

DESCRIPTION OF THE PREFERRED EMBODIMENT

An electrophoresis apparatus 10 embodying the invention is illustrated in the drawings. As shown in FIG. 1, the apparatus 10 comprises, generally, a sequencing cell 12, a fluid circulator and temperature regulator 14, also known as a thermal regulator, a power supply 16, and a gel dryer 17. The sequencing cell 12 is preferably the same as is described in copending application Ser. No 820,508, which is titled "Electrophoresis Apparatus," which was filed concurrently herewith, which is assignee to the assignee hereof, and which is incorporated herein by reference now Pat. No. 5,242,568 granted Sep. 7, 1993. The cell 12 includes a cooling jacket (not shown) having an inlet and on outlet. The power supply 16 and gel dryer 17 are conventional and will not be described in greater detail.

Figure 2:
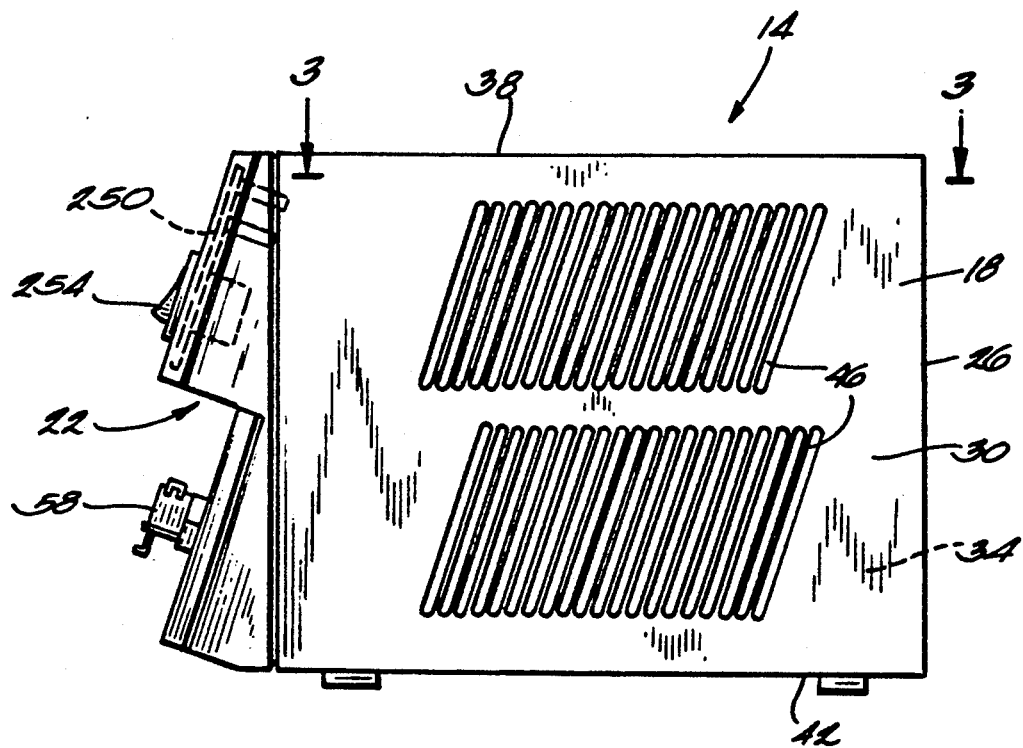
FIG. 2 is a side elevational view, partially broken away, of the fluid circulator and temperature regulator.
Figure 3:
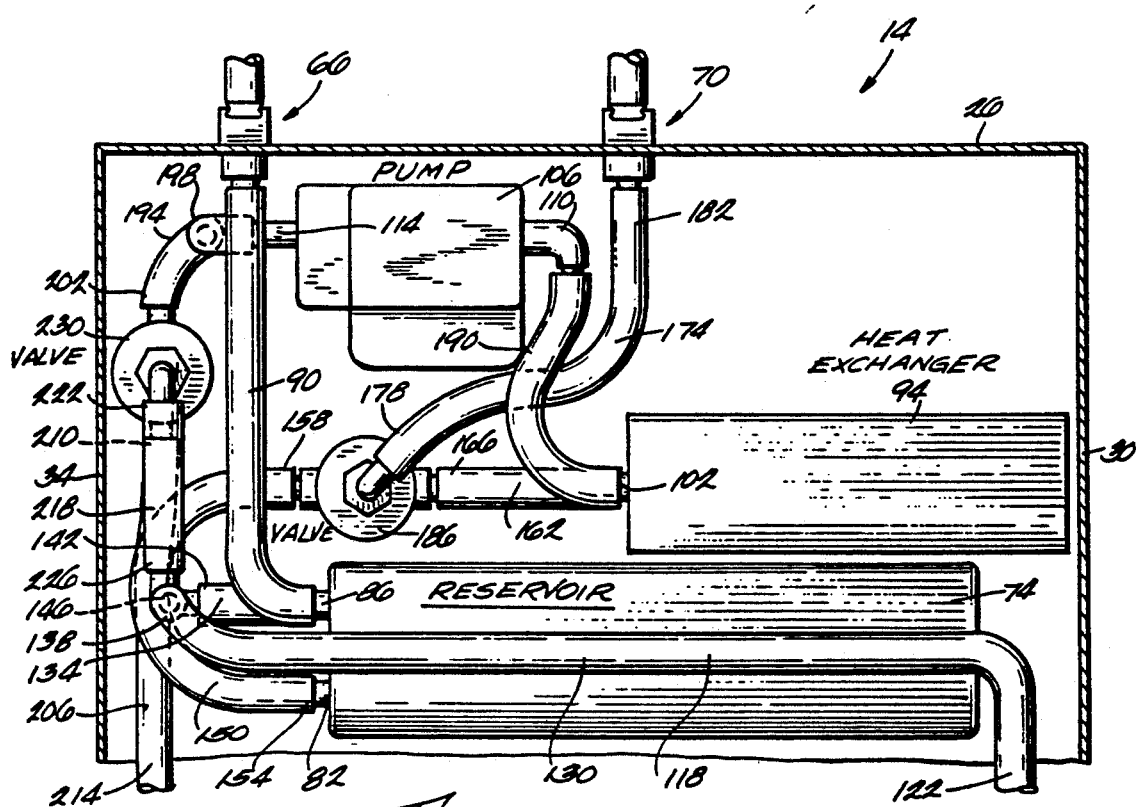
FIG. 3 is a view taken along line 3—3 in FIG. 2.

The fluid circulator 14 comprises (see FIGS. 1-3) a generally rectangular housing 18 including a front panel 22, a rear wall 26, opposite side walls 30 and 34, a top wall 38, and a bottom wall 42. The side walls 30 and 34 have therein vent openings 46. The front panel 22 has thereon an outlet connector 50 which, in FIG. 1, is connected to the cooling jacket inlet via a flexible conduit 54. The front panel 22 also has thereon an inlet connector 58 which, in FIG. 1, is connected to the cooling jacket outlet via a flexible conduit 62. Alternatively, the connectors 50 and 58 can be connected to each other by either conduit 54 or conduit 62. Each of the connectors 50 and 58 is such that fluid flow through the connector is prevented when a conduit is not in communication with the connector. Such connectors are known in the art and need not be described in greater detail. The rear wall has therein a vent port 66 and an intake port 70.

Figure 4:
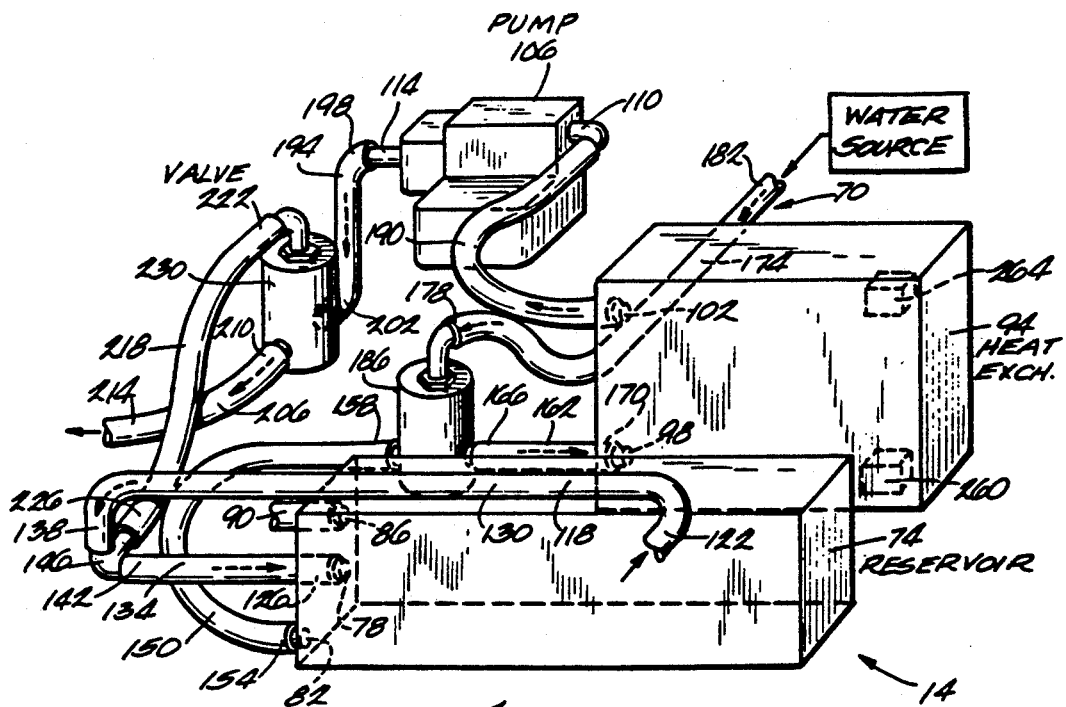
FIG. 4 is a schematic perspective view of the internal components of the fluid circulator and temperature regulator, showing operation of the fluid circulator and temperature regulator to fill the reservoir.

The fluid circulator 14 also comprises (see FIGS. 3 and 4), within the housing 18, a reservoir 74 having a cooling fluid inlet 78, a cooling fluid outlet 82, and a vent opening 86. The vent opening 86 communicates with the vent port 66 via a vent conduit 90. Also within the housing 18 is a heat exchanger 94 having a cooling fluid inlet 98 and a cooling fluid outlet 102. The heat exchanger 94 can both cool and heat fluid and is preferably the same as is described in application Ser. No. 674,540, which was filed Mar. 22, 1991, which is assigned to the assignee hereof, and which is incorporated herein by reference.

The fluid circulator 14 also comprises, within the housing 18, a fluid pump 106 having an inlet 110 and an outlet 114. The pump 106 is capable of pumping both air and cooling fluid. Preferably, the pump 106 is a model 14825-641 manufactured by Gorman Rupp Company of Bellville, Ohio.

The fluid circulator 14 further comprises a first conduit 118 having a first end 122 communicating with the inlet connector 58. The first end 122 of the conduit 118 is thus adapted to communicate with the cooling jacket outlet. The conduit 118 also has a second end 126 (FIG. 4) communicating with the reservoir inlet 78. In the illustrated construction, the first conduit 118 includes portions 130 and 134 having respective ends 138 and 142, and the portion ends 138 and 142 are connected by two legs of a T-connector 146. A second conduit 150 has a first end 154 communicating with the reservoir outlet 82 and has a second end 158. A third conduit 162 has a first end 166 and has a second end 170 (FIG. 4) communicating with the heat exchanger inlet 98. A fourth conduit 174 has a first end 178 and has a second end 182 communicating with the intake port 70. The fluid circulator 14 further comprises valve means 186 operable in a first mode for connecting the first end 166 of the third conduit 162 with the second end 158 of the second conduit 150, and operable in a second mode for connecting the first end 166 of the third conduit 162 with the first end 178 of the fourth conduit 174. While various suitable valve means can be employed, in the illustrated construction, the valve means 186 is a conventional solenoid valve that is in the first mode when energized and that is in the second mode when deenergized. The valve 186 is preferably a model 651148 manufactured by KIP Incorporated of Farmington, Conn.

Figure 7:
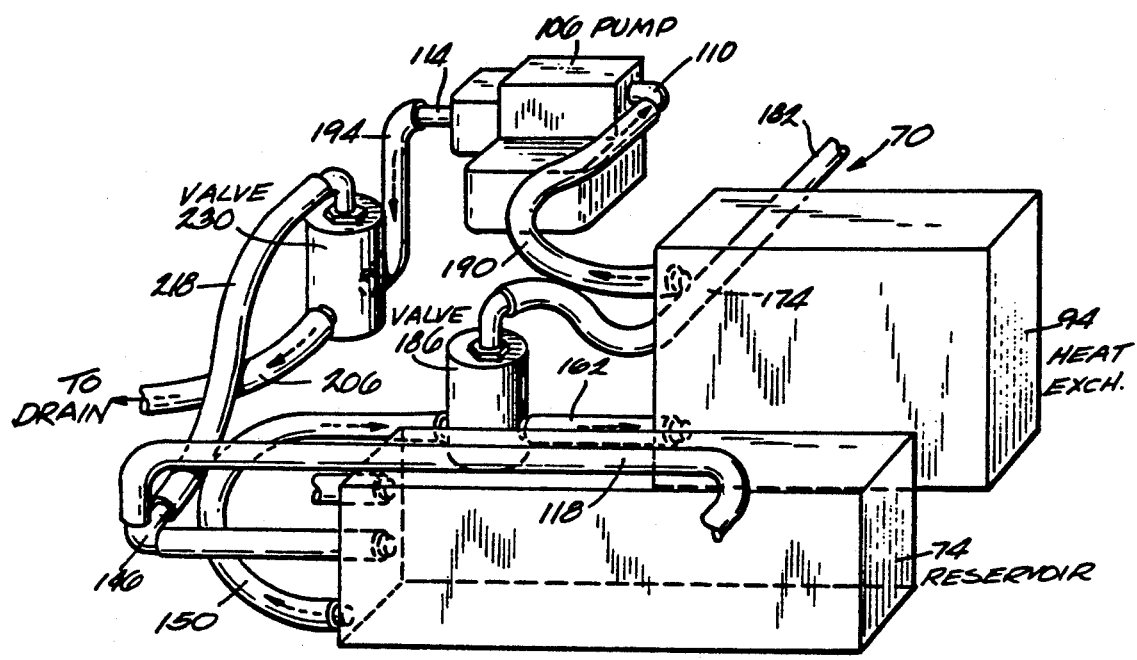
FIG. 7 is a view similar to FIG. 4 showing operation of the fluid circulator and temperature regulator to drain the reservoir.

A fifth conduit 190 communicates between the heat exchanger outlet 102 and the pump inlet 110. A sixth conduit 194 has a first end 198 communicating with the pump outlet 114 and has a second end 202. A seventh conduit 206 has a first end 210 and has a second end 214 communicating with the outlet connector 50. The second end 214 of the seventh conduit 206 thus can be connected to the cell inlet via the hose 54, to the inlet connector 58 via either conduit 54 or conduit 62 communicating between the outlet connector 50 and the inlet connector 58, or to a drain (shown schematically in FIG. 7) via a conduit (not shown) communicating between the outlet connector 50 and the drain.

The fluid circulator 14 further comprises an eighth conduit 218 having a first end 222 and having a second end 226 communicating with the first conduit 118 intermediate the ends of the first conduit 118. In the illustrated construction, the second end 226 of the eighth conduit 218 is connected to the third leg of the T-connector 146. The fluid circulator 14 further comprises valve means 230 operable in a first mode for connecting the second end 202 of the sixth conduit 194 with the first end 210 of the seventh conduit 206, and operable in a second mode for connecting the second end 202 of the sixth conduit 194 with the first end 222 of the eighth conduit 218. The valve means 230 is preferably a solenoid valve substantially identical to the valve 186.

Figure 5:
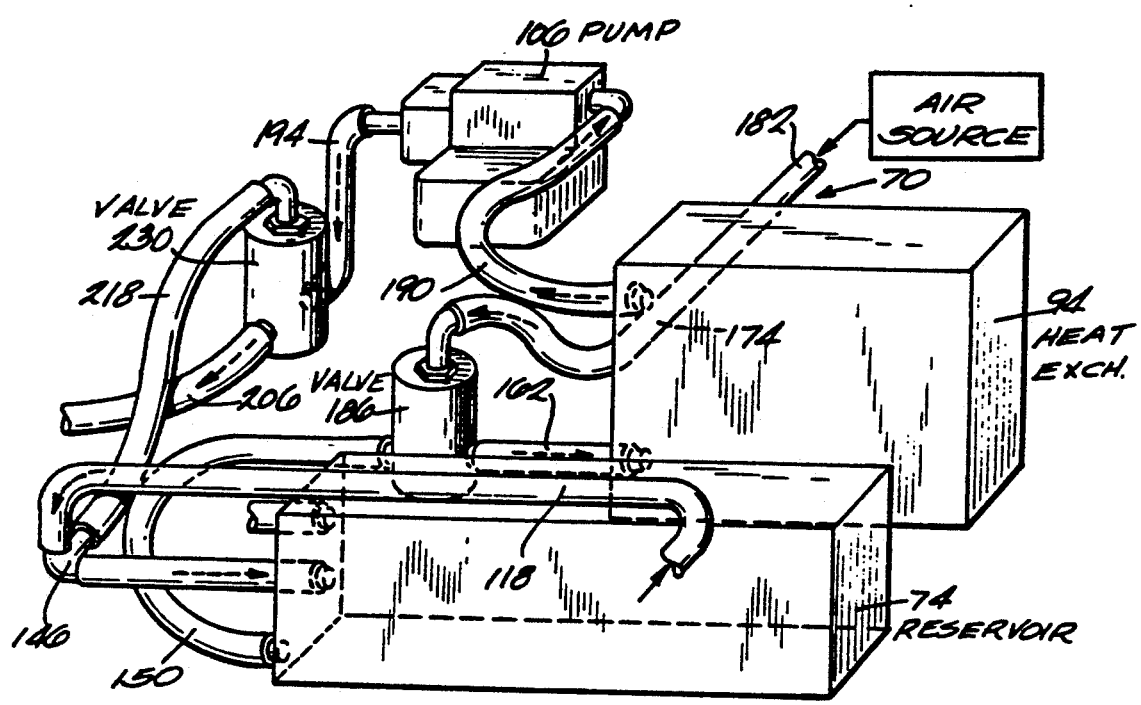
FIG. 5 is a view similar to FIG. 4 showing operation of the fluid circulator and temperature regulator to drain the cell.
Figure 6:
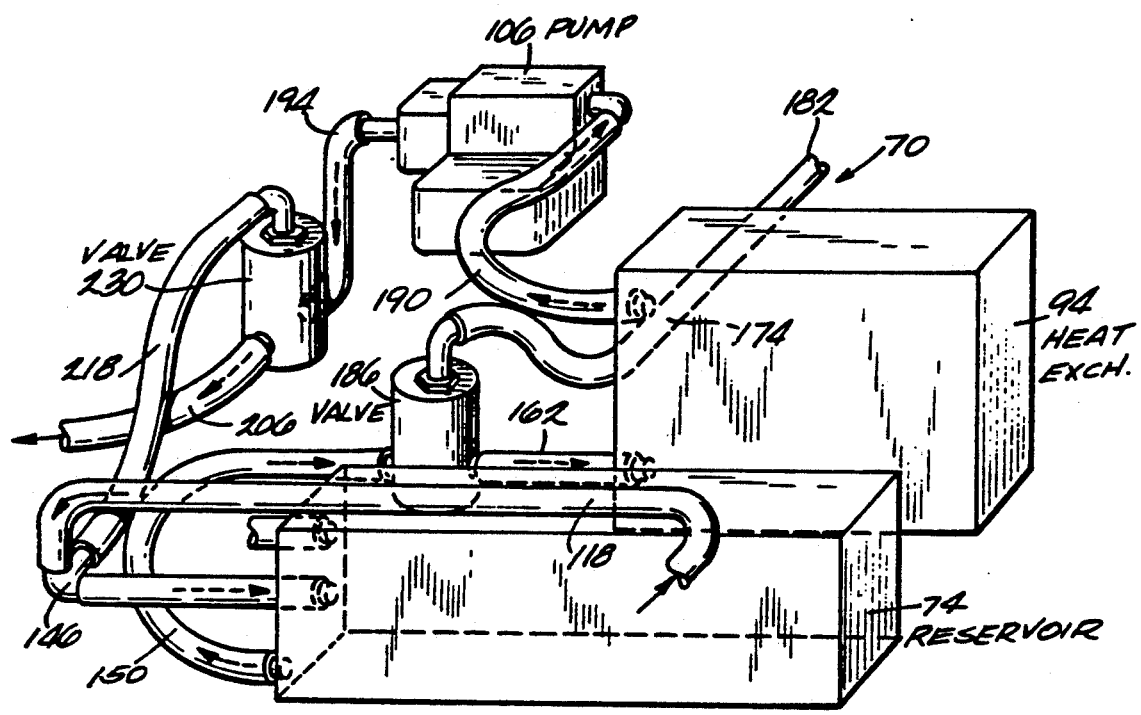
FIG. 6 is a view similar to FIG. 4 showing operation of the fluid circulator and temperature regulator to circulate cooling fluid through the cell.
Figure 8:
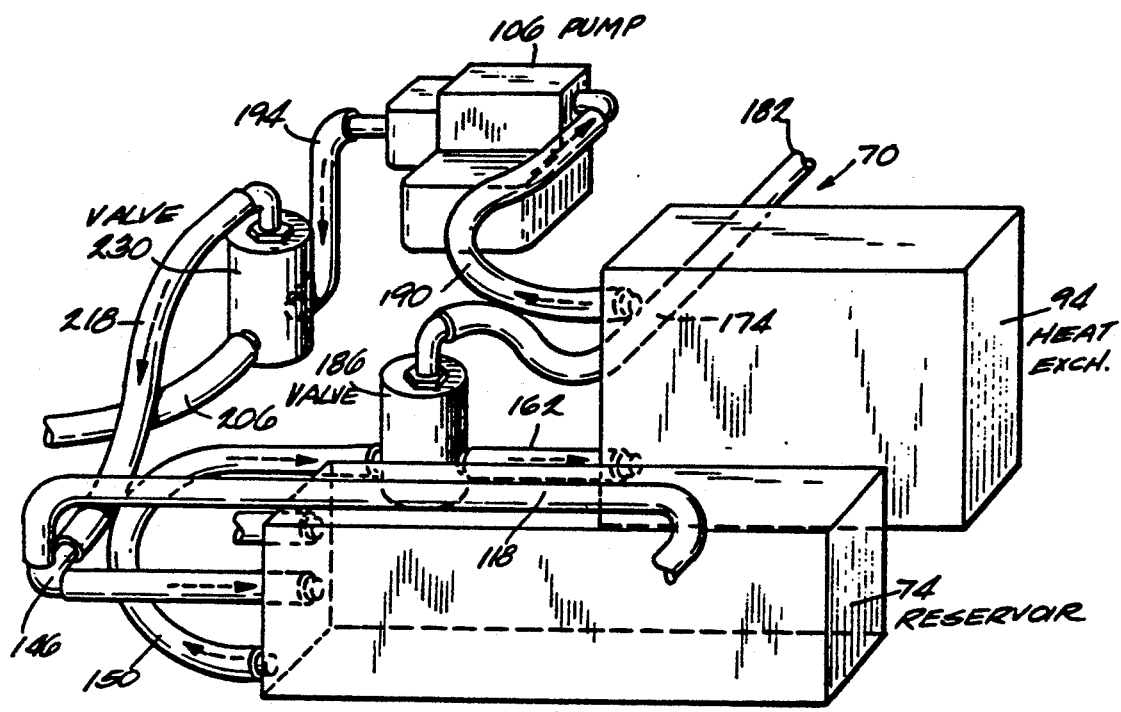
FIG. 8 is a view similar to FIG. 4 showing operation of the fluid circulator and temperature regulator to degasify fluid in the reservoir.

The circulator 14 is operable in a first or empty-cell condition (see FIGS. 4 and 5) wherein the first valve 186 is in its second mode (whereby the first end 166 of the third conduit 162 communicates with the first end 178 of the fourth conduit 174) and the second valve 230 is in its first mode (whereby the second end 202 of the sixth conduit 194 communicates with the first end 210 of the seventh conduit 206). The circulator 14 is also operable in a second or run-cell condition (see FIGS. 6 and 7) wherein the first valve 186 is in its first mode (whereby the second end 158 of the second conduit 150 communicates with the first end 166 of the third conduit 162) and the second valve 230 is in its first mode (whereby the second end 202 of the sixth conduit 194 communicates with the first end 210 of the seventh conduit 206). The circulator 14 is also operable in a third or degasify condition (see FIG. 8) wherein the first valve 186 is in its first mode (whereby the second end 158 of the second conduit 150 communicates with the first end 166 of the third conduit 162) and the second valve 230 is in its second mode (whereby the second end 202 of the sixth conduit 194 communicates with the first end 222 of the eighth conduit 218).

The fluid circulator 14 further comprises (see FIG. 4) means for filling the reservoir 74. The reservoir 74 is filled by operating the circulator 14 in the first condition, with the intake port 70 connected to a source of water (shown schematically in FIG. 4) and with the outlet connector 50 (and thus the second end 214 of the seventh conduit 206) connected to the inlet connector 58 (and thus the first end 122 of the first conduit 118), either via the cooling jacket or via a conduit 54 or conduit 62 extending between the connectors 50 and 58. The circulator 14 fills the reservoir 74 by causing water flow from the water source through the fourth conduit 174, through the third conduit 162, through the heat exchanger 94, through the fifth conduit 190, through the pump 106, through the sixth conduit 194, through the seventh conduit 206, through either the cooling jacket or a conduit extending between the connectors, and through the first conduit 118 to the reservoir 74.

The circulator 14 also comprises (see FIG. 5) means for draining the cooling jacket. The cooling jacket is drained by operating the circulator 14 in the first condition, with the intake port 70 communicating with the atmosphere and with the outlet connector 50 connected to the cooling jacket inlet. The circulator 14 drains the cooling jacket by causing air flow from the atmosphere through the fourth conduit 174, through the third conduit 162, through the heat exchanger 94, through the fifth conduit 190, through the pump 106, through the sixth conduit 194, through the seventh conduit 206, through the cooling jacket, and through the first conduit 118 to the reservoir 74. The air flow pushes fluid out of the cooling jacket and into the reservoir 74.

The circulator 14 further comprises (see FIG. 6) means for circulating cooling fluid through the cooling jacket. Cooling fluid is circulated by operating the circulator 14 in the second condition, with the outlet connector 50 connected to the cooling jacket inlet. The circulator 14 circulates fluid through the cooling jacket and through the heat exchanger 94 by causing fluid flow from the reservoir 74 through the second conduit 150, through the third conduit 162, through the heat exchanger 94, through the fifth conduit 190, through the pump 106, through the sixth conduit 194, through the seventh conduit 206, through the cooling jacket, and through the first conduit 118 to the reservoir 74.

The circulator 14 further comprises (see FIG. 7) means for draining the reservoir 74. The reservoir 74 is drained by operating the circulator 14 in the second condition, with the outlet connector 50 communicating with a drain (schematic in FIG. 7). The circulator 14 drains the reservoir 74 by causing fluid flow from the reservoir 74 through the second conduit 150, through the third conduit 162, through the heat exchanger 94, through the fifth conduit 190, through the pump 106, through the sixth conduit 194, through the seventh conduit 206, and from the outlet connector 50 to the drain.

The circulator 14 further comprises (see FIG. 8) means for degasifying fluid in the reservoir 74. Fluid in the reservoir 74 is degasified by operating the circulator 14 in the third condition. The circulator 14 degasifies fluid in the reservoir 74 by causing fluid flow from the reservoir 74 through the second conduit 150, through the third conduit 162, through the heat exchanger 94, through the fifth conduit 190, through the pump 106, through the sixth conduit 194, through the eighth conduit 218, and to the reservoir 74 through the conduit portion 134.

An important feature of the circulator 14 is that the above-described circulating means, regulating means, degasifying means, and cooling jacket draining means are all operable while the circulator 14 is connected to the cooling jacket. In other words, it is not necessary to disconnect the cooling jacket from the circulator 14 in order to degasify fluid in the reservoir 74 or drain the cooling jacket. The degasifying means is also operable when the circulator 14 is not connected to the cooling jacket. Thus, the degasifying means is operable regardless of whether the circulator 14 is connected to the cooling jacket.

The circulator 14 further comprises (see FIG. 2) a microprocessor 250 for controlling the solenoid valves 186 and 230 and the pump 106. The microprocessor 250 is mounted inside the front panel 22 and is connected to operating switches 254 (FIGS. 1 and 3) and readouts on the front panel 22. The operating switches 254 allow the operator to choose the operating condition (empty-cell, run-cell or degas), to set the desired coolant temperature, and to vary pump speed. The microprocessor 250 includes an interlock switch or connector (not shown) that is operably connected to the power supply 16. The interlock switch is normally closed when the circulator 14 is in the run-cell condition, so that the power supply 16 outputs voltage. The interlock switch is open when the circulator 14 is in either the empty-cell or degas condition, so that the power supply 16 does not output voltage. As a result, the operator cannot run the cell 12 unless the circulator 14 is in the run-cell condition.

Means are provided for preventing fluid flow to the cooling jacket when the volume of fluid in the reservoir 74 falls below a first predetermined level. This means preferably includes a conventional low-limit float switch 260 (shown schematically and in phantom in FIG. 3) located in the reservoir 74. The switch 260 is normally closed and opens when the fluid in the reservoir 74 falls below the first level. Opening of the switch 260 closes or disables the interlock switch and also shuts off the pump 106. This prevents the pump 106 from pumping air to the cooling jacket and also prevents operation of the cell 12.

Means are also provided for preventing fluid flow to the reservoir 74 when the volume of fluid in the reservoir 74 reaches a predetermined second level. This means preferably includes a conventional high-limit float switch 264 (shown schematically and in phantom in FIG. 3) located in the reservoir 74. The switch 264 is normally closed and opens when the fluid level in the reservoir 74 reaches the second level. Opening of the switch 264 shuts off the pump 106 and thereby prevents overfilling of the reservoir 74.

Various features of the invention are set forth in the following claims.

We claim:

1. A fluid circulator and temperature regulator apparatus for use in an electrophoresis process with a sequencing cell including a cooling jacket having an inlet and an outlet, said apparatus being adapted to be connected to the cooling jacket inlet and outlet, and said apparatus comprising a reservoir having an inlet and an outlet, means for circulating cooling fluid through the cooling jacket, said circulating means including a fluid pump having an outlet adapted to communicate with the cooling jacket inlet, means for regulating the temperature of the cooling fluid, means for degasifying fluid in said reservoir, a first conduit having a first end adapted to communicate with the cooling jacket outlet and having a second end communicating with said reservoir inlet, a heat exchanger having an inlet and an outlet, an intake port, a second conduit having a first end communicating with said reservoir outlet and having a second end, a third conduit having a first end and having a second end communicating with said heat exchanger inlet, a fourth conduit having a first end and having a second end communicating with said intake port, first valve means operable in a first mode for connecting said first end of said third conduit with said second end of said second conduit, and operable in a second mode for connecting said first end of said third conduit with said first end of said fourth conduit, a fifth conduit communicating between said heat exchanger outlet and said pump inlet, a sixth conduit having a first end communicating with said pump outlet and having a second end, a seventh conduit having a first end, an eighth conduit having a first end and having a second end communicating with said first conduit intermediate said ends of said first conduit, and second valve means operable in a first mode for connecting said second end of said sixth conduit with said first end of said seventh conduit, and operable in a second mode for connecting said second end of said sixth conduit with said first end of said eighth conduit.

2. Apparatus as set forth in claim 1 wherein said apparatus is operable in a first condition wherein said first valve means is in said second mode and said second valve means is in said first mode, a second condition wherein said first valve means is in said first mode and said second valve means is in said first mode, and a third condition wherein said first valve means is in said first mode and said second valve means is in said second mode.

3. Apparatus as set forth in claim 2 wherein said seventh conduit has a second end, wherein said apparatus is operable in said first condition, with said intake port connected to a source of water and with said second end of said seventh conduit connected to said first end of said first conduit, either via the cooling jacket or via a patch tube, to fill said reservoir by causing water flow from the water source through said fourth conduit, through said third conduit, through said heat exchanger, through said fifth conduit, through said pump, through said sixth conduit, through said seventh conduit, and through said first conduit to said reservoir.

4. Apparatus as set forth in claim 2 wherein said seventh conduit has a second end, wherein said apparatus is operable in said first condition, with said intake port communicating with the atmosphere and with said second end of said seventh conduit connected to the cooling jacket inlet, to drain the cooling jacket by causing air flow from the atmosphere through said fourth conduit, through said third conduit, through said heat exchanger, through said fifth conduit, through said pump, through said sixth conduit, through said seventh conduit, through the cooling jacket, and through said first conduit to said reservoir, whereby said air flow pushes fluid out of the cooling jacket and into said reservoir.

5. Apparatus as set forth in claim 2 wherein said seventh conduit has a second end, wherein said apparatus is operable in said second condition, with said second end of said seventh conduit connected to the cooling jacket inlet, to circulate fluid through the cooling jacket and through said heat exchanger by causing fluid flow from said reservoir through said second conduit, through said third conduit, through said heat exchanger, through said fifth conduit, through said pump, through said sixth conduit, through said seventh conduit, through the cooling jacket, and through said first conduit to said reservoir.

6. Apparatus as set forth in claim 2 wherein said seventh conduit has a second end, wherein said apparatus is operable in said second condition, with said second end of said seventh conduit connected to a drain, to drain said reservoir by causing fluid flow from said reservoir through said second conduit, through said third conduit, through said heat exchanger, through said fifth conduit, through said pump, through said sixth conduit, and through said seventh conduit to the drain.

7. Apparatus as set forth in claim 2 wherein said apparatus is operable in said third condition to degasify fluid in said reservoir by causing fluid flow from said reservoir through said second conduit, through said third conduit, through said heat exchanger, through said fifth conduit, through said pump, through said sixth conduit, through said eighth conduit, and to said reservoir through the portion of said first conduit extending between said second end of said eighth conduit and said reservoir.

8. A fluid circulator and temperature regulator apparatus for use in an electrophoresis process with a sequencing cell including a cooling jacket having an inlet and an outlet, said apparatus being adapted to be connected to the cooling jacket inlet and outlet, and said apparatus comprising a reservoir, means for circulating cooling fluid through the cooling jacket, said circulating means including a fluid pump having an outlet adapted to communicate with the cooling jacket inlet, means for regulating the temperature of the cooling fluid, means for degasifying fluid in said reservoir, means for preventing fluid flow to the cooling jacket when the volume of fluid in said reservoir falls below a first predetermined level, and means for preventing fluid flow to said reservoir when the volume of fluid in said reservoir reaches a predetermined second level.

9. A fluid circulator and temperature regulator apparatus for use in an electrophoresis process with a sequencing cell including a cooling jacket having an inlet and an outlet, said apparatus being adapted to be connected to the cooling jacket inlet and outlet, and said apparatus comprising a reservoir having an inlet and an outlet, a heat exchanger having an inlet and an outlet, a pump having an inlet and an outlet, an intake port, a first conduit having a first end adapted to communicate with the cooling jacket outlet and having a second end communicating with said reservoir inlet, a second conduit having a first end communicating with said reservoir outlet and having a second end, a third conduit having a first end and having a second end communicating with said heat exchanger inlet, a fourth conduit having a first end and having a second end communicating with said intake port, first valve means operable in a first mode for connecting said first end of said third conduit with said second end of said second conduit, and operable in a second mode for connecting said first end of said third conduit with said first end of said fourth conduit, a fifth conduit communicating between said heat exchanger outlet and said pump inlet, a sixth conduit having a first end communicating with said pump outlet and having a second end, a seventh conduit having a first end and having a second end adapted to communicate with the cooling jacket inlet, an eighth conduit having a first end and having a second end communicating with said first conduit intermediate said ends of said first conduit, and second valve means operable in a first mode for connecting said second end of said sixth conduit with said first end of said seventh conduit, and operable in a second mode for connecting said second end of said sixth conduit with said first end of said eighth conduit, said apparatus being operable in a first condition wherein said first valve means is in said second mode and said second valve means is in said first mode, a second condition wherein said first valve means is in said first mode and said second valve means is in said first mode, and a third condition wherein said first valve means is in said first mode and said second valve means is in said second mode, said apparatus being operable in said first condition, with said intake port connected to a source of water and with said second end of said seventh conduit connected to said first end of said first conduit, either via the cooling jacket or via a patch tube, to fill said reservoir by causing water flow from the water source through said fourth conduit, through said third conduit, through said heat exchanger, through said fifth conduit, through said pump, through said sixth conduit, through said seventh conduit, and through said first conduit to said reservoir, said apparatus being operable in said first condition, with said intake port communicating with the atmosphere and with said second end of said seventh conduit connected to the cooling jacket inlet, to drain the cooling jacket by causing air flow from the atmosphere through said fourth conduit, through said third conduit, through said heat exchanger, through said fifth conduit, through said pump, through said sixth conduit, through said seventh conduit, through the cooling jacket, and through said first conduit to said reservoir, whereby said air flow pushes fluid out of the cooling jacket and into said reservoir, said apparatus being operable in said second condition, with said second end of said seventh conduit connected to the cooling jacket inlet, to circulate fluid through the cooling jacket and through said heat exchanger by causing fluid flow from said reservoir through said second conduit, through said third conduit, through said heat exchanger, through said fifth conduit, through said pump, through said sixth conduit, through said seventh conduit, through the cooling jacket, and through said first conduit to said reservoir, said apparatus being operable in said second condition, with said second end of said seventh conduit connected to a drain, to drain said reservoir by causing fluid flow from said reservoir through said second conduit, through said third conduit, through said heat exchanger, through said fifth conduit, through said pump, through said sixth conduit, and through said seventh conduit to the drain, and said apparatus being operable in said third condition to degasify fluid in said reservoir by causing fluid flow from said reservoir through said second conduit, through said third conduit, through said heat exchanger, through said fifth conduit, through said pump, through said sixth conduit, through said eighth conduit, and to said reservoir through the portion of said first conduit extending between said eighth conduit and said reservoir.

10. Apparatus as set forth in claim 9 and further comprising means for preventing fluid flow to the cooling jacket when the volume of fluid in said reservoir falls below a first predetermined level, and means for preventing fluid flow to said reservoir when the volume of fluid in said reservoir reaches a predetermined second level.

* * * * *